(12) United States Patent
Fukuda et al.

(10) Patent No.: US 6,352,642 B1
(45) Date of Patent: Mar. 5, 2002

(54) LEUKOCYTE-REMOVING FILTER MATERIAL

(75) Inventors: Tatsuya Fukuda; Norio Toma, both of Oita (JP)

(73) Assignee: Asahi Medical Co., Ltd. (JP)

( * ) Notice: Subject to any disclaimer, the term of this patent is extended or adjusted under 35 U.S.C. 154(b) by 0 days.

(21) Appl. No.: 09/485,668

(22) PCT Filed: Aug. 25, 1998

(86) PCT No.: PCT/JP98/03762

§ 371 Date: Feb. 11, 2000

§ 102(e) Date: Feb. 11, 2000

(87) PCT Pub. No.: WO99/11304

PCT Pub. Date: Mar. 11, 1999

(30) Foreign Application Priority Data

Aug. 28, 1997 (JP) .............................................. 9-247812

(51) Int. Cl.[7] .............................................. B01D 71/50
(52) U.S. Cl. ............. 210/500.37; 210/490; 210/500.35; 210/645; 210/505
(58) Field of Search ....................... 210/500.35, 500.37, 210/505, 507, 508, 645, 490; 427/244, 245

(56) References Cited

U.S. PATENT DOCUMENTS

| 4,711,793 | A | * | 12/1987 | Ostreicher et al. |
| 5,164,087 | A | * | 11/1992 | Naoi et al. |
| 5,407,581 | A | * | 4/1995 | Onodera et al. |
| 5,498,336 | A | * | 3/1996 | Katsurada et al. |
| 5,501,795 | A | * | 3/1996 | Pall et al. |
| 5,547,576 | A | * | 8/1996 | Onishi et al. |
| 5,616,254 | A | * | 4/1997 | Pall et al. |
| 6,045,694 | A | * | 4/2000 | Wang et al. |

FOREIGN PATENT DOCUMENTS

| EP | 267286 A | 10/1987 |
| EP | 0500472 A2 | 8/1992 |
| EP | 606646 A | 7/1994 |
| JP | 6/247862 | 9/1964 |
| JP | 1/249063 | 10/1989 |
| WO | WO 87/05812 | 10/1987 |

* cited by examiner

*Primary Examiner*—Ana Fortuna
(74) *Attorney, Agent, or Firm*—Pennie & Edmonds LLP (57) ABSTRACT

A leukocyte-removing filter medium for removing leukocytes from a leukocyte-containing fluid, wherein said filter medium has, at least on its surface, hydrophilic basic groups containing at least one nonionic hydrophilic portion and at least one basic portion, in which said hydrophilic portion(s) is located nearer to the end of the hydrophilic basic group than said basic portion(s) is.

16 Claims, 1 Drawing Sheet

LEUKOCYTE-REMOVING FILTER MATERIAL

TECHNICAL FIELD

The present invention relates to a leukocyte-removing filter medium for removing leukocytes from a leukocyte-containing fluid such as a whole blood product or a red cell concentrate, and a method for removing leukocytes by the use of the leukocyte-removing filter medium.

BACKGROUND ART

In the field of blood transfusion, in addition to so-called whole blood transfusion comprising transfusing a whole blood product obtained by adding an anticoagulant to blood collected from a blood donor, so-called component transfusion comprising separating a blood component necessary to a blood recipient from the whole blood product and transfusing the blood component is generally carried out. The component transfusion is classified into red cell transfusion, platelet transfusion, plasma transfusion, etc. according to the species of blood component necessary to a blood recipient. Blood component products used in these blood transfusions include red cell products, platelet products, plasma products, etc. In recent years, a so-called leukocyte-free blood transfusion has been commonly used in which a blood product is transfused after being freed of leukocytes contained therein as contaminants. This is because it has been revealed that relatively slight side effects accompanying blood transfusion, such as headache, nausea, chill, non-hemolytic pyretic reaction, etc., and serious side effects such as alloantigen sensitization, viral infection, post transfusion GVHD, etc., which have serious influences on a blood recipient, are caused mainly by leukocytes contained as contaminants in a blood product used in transfusion.

It is said that to prevent the relatively slight side effects such as headache, nausea, chill, pyrexia, etc., it is sufficient that leukocytes in a blood product are removed until their residual ratio becomes less than $10^{-1}$–$10^{-2}$. It is also said that to prevent the serious side effects such as alloantigen sensitization, viral infection, etc., it is sufficient that leukocytes are removed until their residual ratio becomes less than $10^{-4}$–$10^{-6}$.

Methods for removing leukocytes from a blood product are divided broadly into two categories, i.e., centrifugation methods in which leukocytes are separated and removed with a centrifuge by utilizing the difference in specific gravity among blood components, and filter methods in which leukocytes are removed by using a filter medium composed of a fibrous material or a porous element such as a porous material having intercommunicating voids. The filter methods have been commonly used at present because they have advantages such as excellent leukocyte-removing capability, easy operations, and low cost. Of the filter methods, a method of removing leukocytes by adhesion or adsorption using, as a filter medium, a nonwoven fabric or a porous material having intercommunicating voids, is the most widespread at present because of its especially excellent leukocyte-removing capability.

As to the mechanism of the removal of leukocytes by the use of the above-mentioned filter medium composed of a fibrous material or a porous material, it is considered that the removal is caused mainly because leukocytes brought into contact with the filter medium surface are adhered to or adsorbed on the filter medium surface. Therefore, increasing the frequency of collision between the filter medium and leukocytes, i.e., reducing the fiber diameter or the pore size of the filter medium or increasing the packing density of the filter medium in an filter apparatus, has been investigated as a means for improving the leukocyte-removing capability of conventional filter media. However, there has been a limit in the improvement of the leukocyte-removing capability by the use of only the above means in the case of a product having a high red cell content, such as a whole blood product or a red cell product. That is, the frequency of contact of red cells, containted at a high concentration in the product, with the filter medium and the resistance to fluid passage increase, with an increase of the frequency of contact of leukocytes with the filter medium. Thus, there have been problems such as the prolonged treatment time and hemolysis due to the breakage of red cell membrane.

On the other hand, investigations have been conducted based on the knowledge of surface chemical properties of filter media. JP-A-1/249063 discloses a filter medium having a hydrophilic and negatively charged surface. WO 87/05812 discloses a filter medium containing nonionic hydrophilic groups and basic nitrogen-containing functional groups and having a content of the basic nitrogen-containing functional groups of less than 4.0% by weight and not less than 0.2% by weight. These techniques, however, are intended for maintaining the leukocyte-removing capability while improving the passage rate of platelets known as very adhesive cells, and hardly make further improvement in the leukocyte-removing capability. The technique disclosed in EP 0500472-A2 is not intended for increasing the removal rate of leukocytes but for increasing the removal rate of platelets while maintaining a satisfactory capability of passing red cells, by using a filter medium with a positive zeta potential in the removal of leukocytes and platelets from a red cell product. JP-A-6/24782 discloses a filter medium which contains basic functional groups and nonionic hydrophilic groups, has a molar ratio of the basic functional groups to the nonionic hydrophilic groups of less than 6 and not less than 0.6, and contains the basic functional groups at a density of less than 0.1 meq/m$^2$ and not less than 5×10$^{-5}$ meq/m$^2$. This filter medium, however, does not have sufficient inhibitory effect on the adhesion of red cells and hardly makes stable improvement in the leukocyte-removing capability.

DISCLOSURE OF THE INVENTION

A first object of the present invention is to provide a filter medium which suppresses the adhesion of red cells thereto, has a very high affinity for leukocytes, has an especially high leukocyte-removing capability, permits a satisfactory flow of a leukocyte-containing fluid, and has an excellent blood compatibility. This filter medium has, at least on its surface, hydrophilic basic groups containing at least one nonionic hydrophilic portion and at least one basic portion, in which said hydrophilic portion(s) is located nearer to the end of the hydrophilic basic group than said basic portion(s) is. The present inventors found that the above first object can be achieved by using such a leukocyte-removing filter medium.

That is, the present invention relates to a leukocyte-removing filter medium for removing leukocytes from a leukocyte-containing fluid, wherein the filter medium has, at least on its surface, hydrophilic basic groups containing at least one nonionic hydrophilic portion and at least one basic portion, in which the hydrophilic portion(s) is located nearer to the end of the hydrophilic basic group than said basic portion(s) is.

A second object of the present invention is to provide a method for removing leukocytes with a very high efficiency from a leukocyte-containing fluid such as a whole blood product, a red cell concentrate or the like while suppressing the adhesion of red cells. The present inventors found that the above second object can be achieved by using an apparatus comprising at least an inlet, a filter comprising the leukocyte-removing filter medium of the present invention properly located therein, and an outlet, thereby introducing a leukocyte-containing fluid through the inlet, and recovering through the outlet the fluid filtered through the filter.

That is, the present invention relates to a method for removing leukocytes from a leukocyte-containing fluid, which comprises using an apparatus comprising at least 1) an inlet, 2) a filter comprising the leukocyte-removing filter medium of claim 1 and 3) an outlet, wherein the method comprises introducing the leukocyte-containing fluid through the inlet, and recovering through the outlet the fluid filtered through said filter.

BEST MODE FOR CARRYING OUT THE INVENTION

The leukocyte-removing filter medium of the present invention comprises a base material forming the filter medium and hydrophilic basic groups on the base material surface, the hydrophilic portion(s) of which is located nearer to the end of the hydrophilic basic group than the basic portion(s) is. The filter medium of the present invention includes any filter medium having such a structure, so long as its hydrophilic basic groups on the surface have at least one hydrophilic portion in the vicinity of the end (terminal region) of the hydrophilic basic group, even if the hydrophilic basic group has a hydrophilic portion in a region other than the terminal region. The phrase "comprises hydrophilic basic groups on the base material surface" used here means that a monomer containing one or more hydrophilic basic groups or a polymer containing hydrophilic basic groups has been introduced onto the surface of the base material which forms the filter medium, by any well-known method such as by a covalent bond, ionic bond, physical adsorption, embedding, precipitate insolubilization, etc. so as not to be released, or that the base material which forms the filter medium is formed of a polymer (or macromolecular) material having hydrophilic basic groups, so that the hydrophilic basic groups may be present on the surface of the base material. In both cases, the filter medium of the present invention includes the resulting filter medium.

In addition, the term "the terminal region of the hydrophilic basic group" used herein means a region at a distance farther than the distance (length) from a portion holding the hydrophilic basic group (hereinafter referred to also as the holding portion) to the basic portion in the formula representing the chemical structure of the filter medium surface. Here, the term "holding portion" means a portion where the hydrophilic basic group is in contact with the base material which forms the filter medium. Specifically, for example, when hydrophilic basic groups themselves, via a monomer containing one or more hydrophilic basic groups, or a polymer containing hydrophilic basic groups, are introduced onto the base material which forms the filter medium, by a covalent bond, ionic bond or the like, the portion where the hydrophilic basic group is bonded to the base material is called the holding portion. When a polymer obtained by using a polymerizable monomer containing one or more hydrophilic basic groups is introduced onto the surface of the base material which forms the filter medium, by physical adsorption through a coating or the like, the main chain of the polymer is called the holding portion. When the filter medium is formed of a polymer (or macromolecular) material having hydrophilic basic groups as side chains, the portion where the side chain binds to the main chain of the polymer (or macromolecular) material is called the holding portion.

That is, the leukocyte-removing filter medium of the present invention is a filter medium having, on its surface, hydrophilic basic groups having such a specific structure that at least one hydrophilic portion is located in a region where, (upon contacting the filter medium with blood) the hydrophilic portion(s) comes into contact with blood cells such as red cells and leukocytes contained in the blood, more easily than the basic portion(s) of the hydrophilic basic group does.

Figure 1:
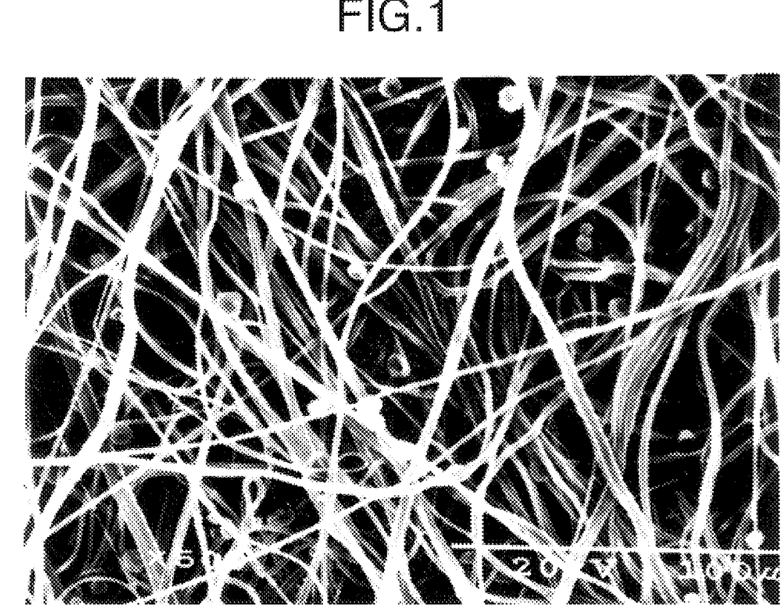
FIG. 1 is an electron micrograph of the leukocyte-removing filter medium of the present invention taken after the filtration of blood through the filter medium.

The following was found: surprisingly, by introducing hydrophilic basic groups having such a structural characteristic onto the surface of a filter medium, an inhibitory effect on the adhesion of red cells is brought about, and there is obtained a leukocyte-removing filter medium which has a very high affinity for leukocytes and does not prolong the blood treatment time. It will be clear from the electron micrograph shown in FIG. 1 that red cells hardly adhere to the leukocyte-removing filter medium of the present invention.

Figure 2:
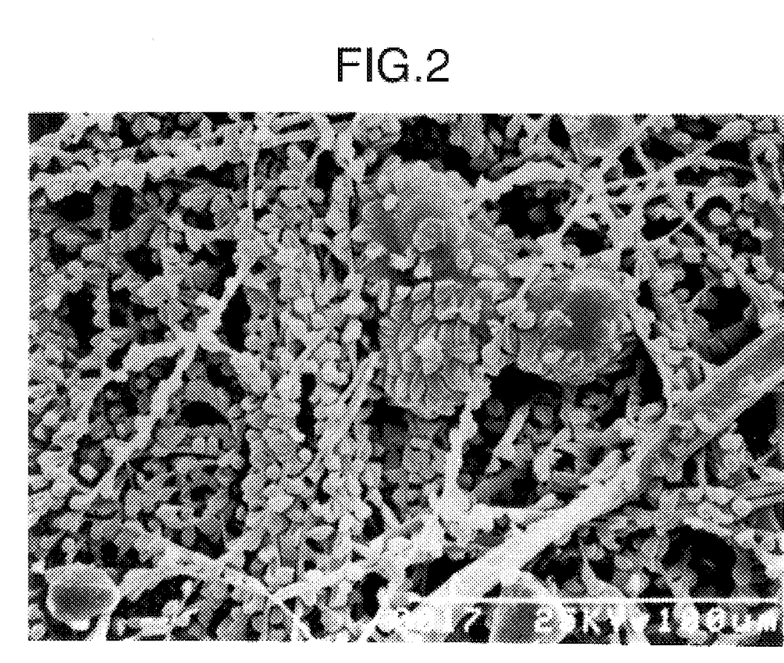
FIG. 2 is an electron micrograph of a filter medium having a large amount of red cells adhering thereto, which was taken after the filtration of blood through the filter medium.

On the other hand, when the present inventors investigated the filtration of a red cell concentrate having an especially low protein concentration using a filter medium which had hydrophilic portions and basic portions independently on the surface but had no hydrophilic basic group unlike in the present invention, that is, specifically a filter medium coated with polymers which had been obtained from polymerizable monomers having a dialkylamino group and those from polymerizable monomers having a hydroxyl group with a high content of units of the polymerizable monomer having a dialkylamino group, phenomena such as the prolongation of the treatment time and deterioration of the leukocyte-removing capability were observed. When the filter medium which had showed such phenomena was observed by an electron microscope, the adhesion of a large amount of red cells to the filter medium surface was observed as shown in FIG. 2. Since a whole blood product or a red cell product such as the red cell concentrate contains about 1,000 times as many red cells as leukocytes, it is conjectured that a large amount of red cells adhered to the filter medium plugging the pores of the filter medium, thereby prolonging the treatment time. It is also conjectured that red cells also adhered to the adsorption sites of the filter medium on which leukocytes should have been originally adsorbed, and thus the leukocyte-removing capability was deteriorated. The following was also found: when the content of dialkylamino groups in the above-mentioned polymer is reduced, the adhesion of red cells can be suppressed although it is difficult to improve the leukocyte-removing capability as expected.

Although the reason why the leukocyte-removing filter medium of the present invention exhibits the very excellent performance characteristics described above has not yet become apparent, it can be speculated that they may be exhibited by the following mechanism. A material having nonionic hydrophilic portions such as hydroxyl groups, poly(ethylene oxide) chains or the like tend to suppress the adhesion of blood cells. On the other hand, basic portions can adsorb cells by electrostatic action owing to their positive charges. It is conjectured that the adhesion of red cells in the basic portions is suppressed by placing such a nonionic hydrophilic portion(s) as above in the terminal region of the hydrophilic basic group so that the nonionic hydrophilic portion(s) may come into contact with cells more often than the basic portion(s) may. On the other hand, since leukocytes are more adhesive than red cells and are larger than red cells, they are subject to the electrostatic-attraction-like action of the basic portion(s). Thus, it is conjectured that leukocytes are efficiently and selectively adsorbed on the basic portions.

Furthermore, the filter medium having hydrophilic basic groups on the surface of the present invention seems to have a very high affinity for leukocytes and an inhibitory effect on the release of leukocytes once adsorbed on the filter medium. This can be conjectured from the following fact: when the filter medium having hydrophilic basic groups on the surface of the present invention was compared with a filter medium having basic groups such as dialkylamino groups on the surface, in an experimental system in which the adhesion of red cells could be hardly caused, namely, where the influence of the adhesion of red cells is excluded, the filter medium of the present invention having hydrophilic basic groups on the surface had a significantly higher leukocyte-removing capability than the other, though the density of the hydrophilic basic groups introduced on the surface of this filter medium and the density of the basic groups introduced on the surface of the other filter medium were substantially the same.

That is, the introduction of hydrophilic basic groups having the specific structure onto the surface of a filter medium, which was found in the present invention, is very important in preventing the adhesion of red cells as well as the deterioration of the leukocyte-removing capability and the prolongation of the treatment time which are considered to be attributable to the adhesion of red cells, and in greatly improving the affinity for leukocytes.

In addition, in the hydrophilic basic group according to the present invention, the hydrophilic portion(s) is preferably located at the extreme end of the hydrophilic basic group. This is because the inhibitory effect on the adhesion of red cells tends to be enhanced by the location of the hydrophilic portion(s) at the extreme end of the hydrophilic basic group.

It was found that the leukocyte-removing filter medium of the present invention has an excellent blood compatibility. Nonionic hydrophilic portions such as hydroxyl groups tend to induce the complement activation, but the leukocyte-removing filter medium of the present invention hardly caused the complement activation. Moreover, the leukocyte-removing filter medium of the present invention had such a very good blood compatibility that it adsorbed only a slight amount of coagulation factors represented by Factor VIII, and hardly caused hemolysis.

The term "nonionic hydrophilic portion" used herein means a portion having a structure which is very difficult to inonize and has a highly hydrophilic morphology. The introduction of the nonionic hydrophilic portions facilitates wetting of the filter medium surface at the time of contact of the surface with the blood and hence is effective in preventing a one-sided flow of the blood. Consequently, the blood flow area in the filter medium is increased, and thus the introduction of such portions can contribute also to the enhancement of the leukocyte-removing capability of the filter medium.

Specific examples of the nonionic hydrophilic portion referred to herein are hydroxyl groups, amide groups, ether group, nitro group, nitro so group, sulfoxide group, sulfonyl group, phosphoryl group, phospho group, carboxamide, sulfonamide, thio acid amide, cyano group, cyanate, thiocyanate, isothiocyanate, etc. of these, especially preferable are hydroxyl group, amide group and ether groups such as a poly(ethylene oxide) chain having a number of ethylene oxide repeating units of not more than 10 and not less than 2, which are chemically stable and highly hydrophilic. Hydroxyl group is the most preferable.

The term "basic portion" used herein means a portion having a positive charge. Because of its positive charge, the basic portion is effective in adsorbing negatively charged leukocytes under physiological conditions by electrostatic interaction, and hence can improve the affinity for leukocytes.

Specific examples of the basic portion usable in the present invention are secondary amino group, tertiary amino group, quaternary amino group, and nitrogen-containing heterocyclic groups having a skeleton of pyrrole, pyrazole, pyrrolidine, piperidine or the like. Of these, secondary and tertiary amino groups are preferable because they are chemically stable and are very safe when used in medical appliances.

The term "hydrophilic basic group" used herein means a functional group having a structure comprising the above-mentioned nonionic hydrophilic portion(s) and basic portion (s) . More specifically, the term means a functional group represented by the following formula (1) or (2):

Formula (1)

Formula (2)

wherein $R^1$: a structure containing a hydrophilic portion, $R^2$ and $R^3$: a structure containing a hydrophilic portion, or a structure having no hydrophilic portion such as alkyl group or hydrogen.

Of such hydrophilic basic groups, preferable are mono-hydroxyalkylamino groups, bis(hydroxyalkyl)amino groups and tris (hydroxyalkyl) amino groups, which are formed by bonding of at least one hydroxyl group to a positively charged nitrogen atom through one or more carbon atoms. In addition, the number of carbon atoms of the alkyl portion in the hydroxyalkylamino structure is preferably not more than 10 and not less than 1, more preferably not more than 5 and not less than 1.

A method for introducing the hydrophilic basic groups according to the present invention onto the surface of the base material which forms the filter medium is not particularly limited, and various well-known methods may be adopted. The method includes, for example, a method comprising introducing a monomer having one or more hydrophilic basic groups by a grafting method such as radiation grafting or plasma grafting, a method comprising coating with a polymer having hydrophilic basic groups, and a method comprising reacting active groups on the base material surface with a chemical species such as a monomer having one or more hydrophilic basic groups or a polymer having hydrophilic basic groups.

The polymerizable monomer having one or more hydrophilic basic groups which can be used in the grafting method or the polymer coating method includes, for example, (meth) acrylic acid derivatives such as N-mono(hydroxyalkyl) aminoethyl (meth)acrylate, N,N-bis(hydroxyalkyl) aminoethyl (meth)acrylate, N-mono(hydroxyalkyl)amino-2-hydroxypropyl (meth)acrylate, N,N-bis(hydroxyalkyl) amino-2-hydroxypropyl (meth)acrylate, N-(methoxypolyoxyethyl)aminoethyl (meth)acrylate, N,N-bis(methoxypolyoxyethyl)aminoethyl (meth)acrylate, etc.; styrene derivatives such as N-hydroxyaminostyrene, etc.; and vinyl derivatives such as N-(hydroxyalkyl)-aminoethylenes, etc. In the present specification, the word "(meth) acrylate" stands for acrylate or methacrylate and the word "(meth)acrylic acid" stands for acrylic acid or methacrylic acid. Of the above-exemplified monomers, the (meth)acrylic acid derivatives are preferable because of their easy synthesis and excellent handleability. Of the (meth) acrylic acid derivatives, those having a mono(hydroxyalkyl) amino group or a bis(hydroxyalkyl)amino group are more preferable.

When the surface of the base material which forms the filter medium is modified by using the grafting method or the polymer coating method, other polymerizable monomers having no hydrophilic basic group may be introduced onto the surface. As the other polymerizable monomers, any polymerizable monomers may be used without particular limitation, though (meth)acrylic acid derivatives represented by hydroxyethyl (meth)acrylate and methyl (meth)acrylate are preferable because of their excellent handleability.

In addition, when the base material surface is coated with a polymer obtained by using, as monomer components, at least one polymerizable monomer having one or more hydrophilic basic groups and one or more other polymerizable monomers, any copolymer such as a random copolymer, a block copolymer, an alternating copolymer or the like may be used as the polymer, though the random copolymer is preferable because the copolymerization is easy. Although the kinds of the polymerizable monomers for obtaining the above-mentioned copolymer are not particularly limited, a copolymer obtained from two or three kinds of polymerizable monomers is preferable because the production is easy.

As another method for introducing hydrophilic basic groups so that the base material for the leukocyte-removing filter medium of the present invention may have them on the surface, there can be mentioned a method of reacting a chemical species having one or more hydrophilic basic groups, such as a hydroxyalkylamine represented by diethanolamine, with a base material having active groups such as epoxy groups, carboxyl groups, acid halide groups or the like on the surface, to introduce the hydrophilic basic groups. When a base material not having such active groups on the surface is used, the active groups may be introduced onto the surface of the base material by introducing a monomer having the active group, such as glycidyl (meth) acrylate or (meth)acrylic acid, onto the surface of the base material by radiation grafting by means of y-rays, electron rays or the like, or by synthesizing a polymer by use of the above-exemplified monomer having an active group, as a monomer component, and coating the base material surface with this polymer.

Of the various methods described above, the grafting method and the polymer coating method are preferable because they comprise relatively easy operations. In particular, the polymer coating method is a more preferable introduction method because of its excellent productivity.

The density of the hydrophilic basic groups introduced on the surface of the leukocyte-removing filter medium of the present invention is preferably less than 1000 $\mu$eq/m$^2$ and not less than 0.1 $\mu$eq/m$^2$. When the density of the hydrophilic basic groups introduced is less than 0.1 $\mu$eq/m$^2$, the leukocyte-removing capability tends to be undesirably deteriorated. On the other hand, when the density is more than 1000 $\mu$eq/m$^2$, the cost increases undesirably. The density is more preferably less than 100 $\mu$eq/m$^2$ and not less than 0.2 $\mu$eq/m$^2$, still more preferably less than 30 $\mu$eq/m$^2$ and not less than 0.5 $\mu$eq/m$^2$.

The density of the hydrophilic basic groups introduced on the filter medium surface in the present invention can be measured by a well-known method such as X-ray photoelectron spectroscopy (XPS), Auger electron spectroscopy (AES), secondary ion mass spectroscopy (SIMS), attenuated total reflection Fourier transform infrared spectroscopy (ATR-FTIR) or the like. It is also possible to extract substances from the filter medium surface by a suitable method and measure the hydrophilic basic groups contained in the extracted substances by a well-known method such as nuclear magnetic resonance spectroscopy (NMR). The density of the hydrophilic basic groups introduced may be determined also by using acid-base titration or a dye adsorption method. Of the above various methods, the dye adsorption method is preferable because it comprises easy operations. The dye adsorption method comprises adsorbing a dye such as Trypan Blue which has a negative charge, on the basic portion of the hydrophilic basic group, and determining the amount of the hydrophilic basic groups present on the filter medium surface from the amount of the dye adsorbed or the absorbance change caused by the adsorption. More specifically, an aqueous solution containing Trypan Blue and having a pH of about 6 is prepared as an original solution. Then, the filter medium is brought into contact with the original solution at room temperature for 16 hours or more by impregnation with an adequate amount of the original solution. Subsequently, the absorbance of the supernatant after the impregnation of the filter medium with the original solution is measured by the use of visible light having a wavelength of 578 nm, and the density of the hydrophilic basic groups introduced per unit weight of the filter medium or per unit surface area of the filter medium is calculated from the difference between the absorbances of the original solution and the supernatant.

When the density of the hydrophilic basic groups introduced per unit weight of the filter medium is calculated by using the dye adsorption method or any of the other various method described above and the calculated value is converted to the density of the hydrophilic basic groups introduced per unit surface area of the filter medium, the conversion can be carried out by measuring the surface area per unit weight of the filter medium by a mercury injection method and dividing the density of the hydrophilic basic groups introduced per unit weight of the filter medium by the measured value. The surface area per unit weight of the filter medium is measured by the mercury injection method by the following procedure. First, a proper amount of a sample is obtained from each portion of the filter medium which is considered substantially homogeneous, and the weight (W) of the sample is measured. Then, the sample of the filter medium is set in a mercury porosimeter (Poresizer Model 9310 PC 2A of Shimadzu Corp. (Japan) or an apparatus equal thereto in performance characteristics) and its surface area (A) is measured in a pressure range of 0.1 to 180 psia. The surface area per unit weight of the filter medium is calculated by the following equation (I):

$$\text{Surface area per unit weight} = A/W(m^2/g) \qquad (I)$$

In this case, the sampling is carried out in three or more portions of the filter medium and the average of surface area values obtained for the samples, respectively, is taken as the surface area per unit weight of the filter medium.

On the surface of the leukocyte-removing filter medium of the present invention, the ratio of the number of the basic portions to the number of the nonionic hydrophilic portions is preferably less than 0.5 and not less than 0.01. When the ratio of the number of the basic portions to the number of the hydrophilic portions is less than 0.01, it is undesirably almost impossible to obtain a sufficint improving effect on the leukocyte-removing capability. When the ratio of the number of the basic portions to the number of the hydrophilic portions is more than 0.5, the number of adhered red cells tends to increase undesirably. The ratio of the number of the basic portions to the number of the hydrophilic portions is more preferably less than 0.3 and not less than 0.03. When the nonionic hydrophilic portions are poly(ethylene oxide) chains, each poly(ethylene oxide) chain is taken as one hydrophilic portion irrespective of the number of ethylene oxide repeating units, or, the length of the poly(ethylene oxide) chain.

As a base material which forms the filter medium in the present invention, there can be mentioned nonwoven fabrics produced by a melt blow method, a flash spinning method, a paper making method or the like, as well as fiber products such as papers, woven fabrics, knitted fabrics and the like, porous materials (spongy structures) having intercommunicating pores, porous membranes, etc. Of these, the nonwoven fabrics and the porous materials are preferable because they have structures which permit efficient removal of leukocytes.

When the base material which forms the filter medium is made of fibers, the starting fibers include synthetic fibers such as polyamides, polyesters, polyacrylonitriles, polytrifluoroethylenes, poly(methyl methacrylate)s, polystyrenes, polyethylenes, polypropylenes, etc.; regenerated fibers and purified fibers such as cellulose and the like; semisynthetic fibers such as cellulose acetate and the like; natural fibers such as hemp, cotton, silk, etc.; and inorganic fibers such as glass fibers. Of these, the synthetic fibers such as polyesters, polypropylenes, polyethylenes and the like and the regenerated fibers and purified fibers such as cellulose and the like are preferable because of their easy production and easy handling.

In addition, when the fiber is made into the base material, the base material may be either one which comprises fibers having a substantially uniform fiber diameter, or one which comprises a mixture of two or more kinds of fibers having different fiber diameters, such as the base material disclosed in WO 97/23266.

The average fiber diameter of the fibers is preferably less than 3.0 $\mu$m and not less than 0.01 $\mu$m. When the average fiber diameter is less than 0.01 $\mu$m, the mechanical strength of the fibers is undesirably low that the stable production of the filter medium is almost impossible. When the average fiber diameter is 3.0 $\mu$m or more, the frequency of collision between the filter medium and the leukocytes is undesirably low that the effects of the present invention are unlikely to be exerted. The average fiber diameter is more preferably less than 2.0 $\mu$m and not less than 0.1 $\mu$m. The average fiber diameter of the fibers referred to here is determined by the following procedure. Portions which are considered substantially homogeneous are selected as samples from the leukocyte-removing filter medium or the fiber base material which forms the filter, and the samples are photographed by using a scanning electron microscope or the like. In the sampling, the filter medium or the base material is partitioned into sections about 0.5 cm square, and six of the sections are selected at random as samples. Three or more, preferably five or more, portions of each selected section are photographed at a magnification of 2,000 or more. A checkered transparent sheet having lines drawn thereon lengthwise and widthwise at regular intervals of approximately 0.1 mm –10 mm is placed on each photograph. For a fiber at an intersection of the vertical line and the horizontal line, i.e., a lattice point, the fiber width in a direction perpendicular to the fiber axis is measured as the fiber diameter. The measurement is conducted for 50 or more fibers, preferably 100 or more fibers to take an average, which is defined as average fiber diameter. However, data obtained, for example, in the following cases are omitted: the case where a plurality of fibers overlap with one another and the width of the fiber at the intersection cannot be measured because the other fibers obstruct the view of said fiber; and the case where a plurality of fibers form a thick fiber from melting or the like.

When the base material which constitutes the filter medium is a porous material or a porous membrane, a starting material therefor includes polyacrylonitrile, polysulfone, cellulose, cellulose acetate, polyvinyl formal, polyester, poly(meth)acrylate, polyurethane, etc. The average pore size of the porous material or the porous membrane is preferably less than 30 $\mu$m and not less than 1 $\mu$m. When the average pore size is less than 1 $\mu$m, the treatment time is apt to be undesirably prolonged by the resistance to passage of erythrocytes. When the average pore size is more than 30 $\mu$m, the frequency of collision between the filter medium and leukocytes decreases undesirably and the effects of the present invention are unlikely to be exerted. The average pore size is preferably less than 15 $\mu$m and not less than 5 $\mu$m. The average pore size referred to here is a value measured by a mercury injection method. In detail, when the amount of mercury injected at a mercury injection pressure of 0.1 psia is taken as 0% and the amount of mercury injected at a mercury injection pressure of 180 psia as 100%, the average pore size is defined as a pore size corresponding to a mercury injection pressure at which the amount of mercury injected is 50%.

The second object of the present invention is to provide a method for removing leukocytes with a very high efficiency from a leukocyte-containing fluid such as a whole blood product, a red cell concentrate or the like while suppressing the adhesion of red cells. The present inventors earnestly investigated and consequently found that the above second object can be achieved by filtering the leukocyte-containing fluid by the use of an apparatus obtained by properly packing the leukocyte-removing filter medium of the present invention into a container having at least an inlet and an outlet, and recovering the filtered fluid.

The leukocyte-containing fluid to be filtered by the use of the apparatus packed with the leukocyte-removing filter medium of the present invention includes whole blood products, red cell concentrates, platelet concentrates, etc. By filtering such a leukocyte-containing fluid by the use of the apparatus packed with the leukocyte-removing filter medium of the present invention, leukocytes can be efficiently removed, and moreover satisfactory results including the suppression of red cell adhesion can be obtained in the case of a red cell product containing red cells at a concentration of $1 \times 10^9$/mL or more, such as a whole blood product or a red cell concentrate.

When, of red cell products, a red cell concentrate having a plasma protein concentration of 25 g/L or less, in particular, 10 g/L or less is filtered by using the apparatus packed with the leukocyte-removing filter medium of the present invention, a marked inhibitory effect on the adhesion of red cells is particularly exhibited.

When leukocytes are removed simultaneously with blood transfusion at a bedside in a hospital by using the apparatus packed with the leukocyte-removing filter medium of the present invention, a leukocyte-containing fluid is preferably filtered at a rate of less than 15 g/min and not less than 1 g/min. On the other hand, when leukocytes are removed from a blood product for transfusion in a Blood Center or the like by using the apparatus packed with the leukocyte-removing filter medium of the present invention, this leukocyte-containing fluid is preferably filtered at a rate of less than 50 g/min and not less than 15 g/min.

Furthermore, in an extracorporeal circulation therapy for autoimmune diseases, etc., leukocytes can be removed by using the apparatus packed with the leukocyte-removing filter medium of the present invention.

As described above, the leukocyte-removing filter medium of the present invention has a very high affinity for leukocytes and also has an inhibitory effect on the adhesion of red cells, so that it can attain a high leukocyte-removing capability and a satisfactory blood flowability. Moreover, since the filter medium has a very excellent blood compatibility, it can assure ideal safety as a material for medical appliances.

The present invention is illustrated in further detail with reference to the following examples, which should not be construed as limiting the scope of the invention.

EXAMPLE 1

Glycidyl methacrylate was added to toluene (purity 99% (GC), mfd. by Wako Pure Chemical Industries, Ltd.) to a concentration of 1 mol/L, and diethanolamine was slowly dropped into the resulting solution to a concentration of 1.1 mol/L so as not to cause heat generation, to make a total volume of 500 ml. Hydroquinone monomethyl ether (MEHQ) was added thereto as a polymerization inhibitor to a concentration of 0.005 mol/L, and the reaction was carried out at 60° C. for 6 hours. After completion of the reaction, the reaction solution was purified by vacuum distillation, fractional extraction, liquid chromatography and the like. Thus, N,N-bis(hydroxyethyl)amino-2-hydroxypropyl methacrylate (hereinafter referred to as GA) having a hydroxyethylamino group, a hydrophilic basic group was synthesized.

Then, in ethanol (special grade), a polymer was synthesized from the above GA and 2-hydroxyethyl methacrylate (hereinafter referred to as HEMA) by conventional solution radical polymerization. As to the polymerization conditions, the monomer concentration in ethanol was adjusted to 1 mol/L, V-65 (mfd. by Wako Pure Chemical Industries, Ltd.) was added as a polymerization initiator to a concentration of 0.01 mol/L, and the polymerization was carried out under nitrogen at 50° C. for 4.5 hours. After completion of the polymerization, the reaction solution was added dropwise to distilled water to precipitate a polymer, which was then freeze-dried. The GA content of the obtained polymer was measured by acid-base titration to find that the polymer contained about 5 mol % GA units (this polymer is hereinafter referred to as HGA-5).

Polyester nonwoven fabrics with average fiber diameters of about 1.8 $\mu$m and about 1.2 $\mu$m, respectively, produced by a melt blow method were packed into a container having a blood inlet and a blood outlet and having an effective filtration sectional area of 67 mm×67 mm, so that the packing density might be about 0.20 g/cm$^3$. The nonwoven fabric with an average fiber diameter of about 1.8 $\mu$m was located on the blood inlet side to a thickness of about 1.5 mm, and beneath this nonwoven fabric, the nonwoven fabric with an average fiber diameter of about 1.2 $\mu$m was located to a thickness of about 3.0 mm. The container was filled with an ethanolic solution of HGA-5 polymer having a concentration of 0.1% by weight, and allowed to stand for 1 minute. Then, the excess solution was blown off with nitrogen gas and the container was dried in vacuum at 45° C. for 16 hours to produce a filter apparatus. The leukocyte-removing filter medium in the produced filter apparatus had the hydrophilic basic groups on its surface at an average introduction density of 1.7 $\mu$eq m$^2$.

After centrifuging 456 mL of whole blood prepared by adding 56mL of a CPD solution (composition: sodium citrate 26.3 g/L, citric acid 3.27 g/L, glucose 23.20 g/L, sodium dihydrogenphosphate dihydrate 2.51 g/L) as an anticoagulant, to 400 mL of blood the plasma and the buffy coat were removed and 95 mL of a MAP solution (composition: sodium citrate 1.50 g/L, citric acid 0.20 g/L, glucose 7.21 g/L, sodium dihydrogenphosphate dihydrate 0.94 g/L, sodium chloride 4.97 g/L, adenine 0.14 g/L, mannitol 14.57 g/L) as a red cell preservative solution, was added to the residue to prepare a red cell concentrate (hematocrit about 64%, plasma protein concentration about 4 g/L), which was preserved at 4° C. for 10 days. Thereafter, in order to remove minute aggregates contained in the red cell concentrate, it was filtered by using a filter obtained by placing nonwoven fabric with an average fiber diameter of about 33 $\mu$m and nonwoven fabric with an average fiber diameter of about 12 $\mu$m to thicknesses of about 1.2 mm and about 2.3 mm, respectively, from the blood inlet side to the blood outlet side in a container having an effective filtration sectional area of 67 mm×67 mm, so that the packing density was about 0.25 g/cm$^3$.

After 325 g of the red cell concentrate free of minute aggregates were allowed to stand to be adjusted to room temperature of 24° C., the concentrate was filtered through the filter coated with HGA-5, at ahead of 1 m. Before starting the filtration, the filter was connected to a blood bag containing the red cell concentrate, through a blood line, and then the blood bag was pressed by squeezing by hand to force the filter to be filled with the blood. After the filter was thus filled with the blood, the filtration was carried out until the blood was emptied out of the bag, and the filtered blood was recovered. In this case, the filtration time was defined as a time required for the blood to be emptied out of the bag after the blood started flowing out through the outlet of the filter.

The leukocyte concentrations in the red cell concentrate before the filtration (hereinafter referred to as the fluid before filtration) and in the recovered red cell concentrate (hereinafter referred to as the recovered fluid), the volume of the fluid before filtration and that of the recovered fluid were measured, and the leukocyte-removing capability was calculated according to the following equation (II):

Leukocyte-removing capability=−Log{(leukocyte concentration in recovered fluid×volume of recovered fluid)/(leukocyte concentration in fluid before filtration×volume of fluid before filtration)}　　(II)

As the volumes of the fluid before filtration and the recovered fluid, the values obtained by dividing the respective weights by the specific gravity (1.075) of the blood product were taken. The leukocyte concentration of the fluid before filtration was measured by diluting the fluid 10-fold with Turk's solution before filtration, pouring the resulting dilution into a Burker-Turk type hemocytometer, and counting leukocytes under an optical microscope. The leukocyte concentration of the recovered fluid was measured by the following method. The recovered fluid was diluted 5-fold with Leukoplate solution (mfd. by SOBIODA). The diluted solution was thoroughly mixed and then allowed to stand at room temperature for 6 to 10 minutes. The diluted solution was centrifuged at 2,750×g for 6 minutes, and the supernatant was removed to adjust the weight of the residue to 1.02 g. Thus obtained sample fluid was thoroughly mixed and then poured into a Nageotte type hemocytometer, and leukocytes were counted under an optical microscope, there by measuring the leukocyte concentration.

As a result, it was found that the filtration time was 10.4 minutes and the leukocyte-removing capability was 4.45. The filter medium after the filtration of the blood was thoroughly washed with physiological saline, fixed with 0.2% glutaraldehyde, and then freeze-dried. Thus treated filter medium after the filtration of the blood was observed by a scanning electron microscope and it was found that almost no red cell had adhered thereto.

EXAMPLE 2

The process of Example 1 was repeated except that a polymer containing about 25 mol % GA units (hereinafter referred to as HGA-25) was obtained by the same synthetic method as in Example 1 and the filter was coated with HGA-25 by the same method as in Example 1. The average density of hydrophilic basic groups introduced onto the filter medium surface was 7.3 $\mu eq/m^2$, the time required for filtering the blood was 10.2 minutes, and the leukocyte-removing capability was 5.24. The filter medium after the filtration of the blood had almost no red cells adhering thereto.

EXAMPLE 3

The process of Example 1 was repeated except that a polymer containing about 40 mol % GA units (hereinafter referred to as HGA-40) was obtained by the same synthetic method as in Example 1 and the filter was coated with HGA-40 by the same method as in Example 1. The average density of hydrophilic basic groups introduced onto the filter medium surface was 10.6 $\mu eq/m^2$, the time required for filtering the blood was 10.9 minutes, and the leukocyte-removing capability was 5.12. The filter medium after the filtration of the blood had almost no red cells adhering thereto.

EXAMPLE 4

The process of Example 1 was repeated except that a polymer containing about 70 mol % GA units (hereinafter referred to as HGA-70) was obtained by the same synthetic method as in Example 1 and the filter was coated with HGA-70 by the same method as in Example 1. The average density of hydrophilic basic groups introduced onto the filter medium surface was 15.4 $\mu eq/m^2$, the time required for filtering the blood was 11.5 minutes, and the leukocyte-removing capability was 4.93. The filter medium after the filtration of the blood had almost no red cells adhering thereto.

COMPARATIVE EXAMPLE 1

A polymer was synthesized from N,N-diethylaminoethyl methacrylate (hereinafter referred to as DE) and HEMA by the same polymerization method as in Example 1. The DE content of the obtained polymer was about 5 mol % (this polymer is hereinafter referred to as HDE-5). The process of Example 1 was repeated except for coating the filter with this polymer by the same method as in Example 1. The average density of basic groups (diethylamino groups) introduced onto the filter medium surface was 1.8 $\mu eq/m^2$, the time required for filtering the blood was 11.3 minutes, and the leukocyte-removing capability was 3.41. The filter medium after the filtration of the blood had almost no red cells adhering thereto.

COMPARATIVE EXAMPLE 2

The process of Example 1 was repeated except that a polymer containing about 25 mol % DE units (hereinafter referred to as HDE-25) was obtained by the same polymerization method as in Comparative Example 1 and the filter was coated with HDE-25 by the same method as in Example 1. The average density of basic groups introduced onto the filter medium surface was 8.1 $\mu eq/m^2$, the time required for filtering the blood was 35.7 minutes, and the leukocyte-removing capability was 2.84. Red cells adhering to the filter medium after the filtration of the blood were observed.

COMPARATIVE EXAMPLE 3

The process of Example 1 was repeated except that a polymer containing about 40 mol % DE units (hereinafter referred to as HDE-40) was obtained by the same polymerization method as in Comparative Example 1 and the filter was coated with HDE-40 by the same method as in Example 1. The average density of basic groups introduced onto the filter medium surface was 12.3 $\mu eq/m^2$, the time required for filtering the blood was 62.3 minutes, and the leukocyte-removing capability was 2.90. A large amount of red cells adhering to the filter medium after the filtration of the blood were observed.

COMPARATIVE EXAMPLE 4

A polymer was synthesized from N, N-diethylamino-2-hydroxypropyl methacrylate (hereinafter referred to DP) and HEMA by the same polymerization method as in Example 1. The DP content of the obtained polymer was about 40 mol % (this polymer is hereinafter referred to as HDP-40). The process of Example 1 was repeated except for coating the filter with this polymer by the same method as in Example 1. Thus, hydrophilic basic groups having no hydrophilic portion at the end were introduced onto the surface of the filter medium at an average introduction density of 12.0 $\mu eq/m^2$. The time required for filtering the blood was 54.5 minutes, and the leukocyte-removing capability was 2.73. A large amount of red cells adhering to the filter medium after the filtration of the blood were observed.

COMPARATIVE EXAMPLE 5

Through the same filter as in Example 1 except that it had no polymer coating, the same red cell concentrate was filtered by the same procedure as in Example 1. As a result, the blood filtration time was 12.2 minutes, and the leukocyte-removing capability was 3.23. The filter medium after the filtration of the blood had almost no red cells adhering thereto.

Table 1 summarizes the results obtained in Examples 1 to 4 and Comparative Examples 1 to 5.

TABLE 1

| | Coating polymer | Density of hydrophilic basic groups or basic groups ($\mu$eq/m$^2$) | Filtration time (min.) | Leukocyte-removing capability (-Log) | Adhesion of red cells |
|---|---|---|---|---|---|
| Example 1 | HGA-5 | 1.7 | 10.4 | 4.45 | None |
| Example 2 | HGA-25 | 7.3 | 10.2 | 5.24 | None |
| Example 3 | HGA-40 | 10.6 | 10.9 | 5.12 | None |
| Example 4 | HGA-70 | 15.4 | 11.5 | 4.93 | None |
| Comparative Example 1 | HDE-5 | 1.8 | 11.3 | 3.41 | None |
| Comparative Example 2 | HDE-25 | 8.1 | 35.7 | 2.84 | Occurred |
| Comparative Example 3 | HDE-40 | 12.3 | 62.3 | 2.90 | Occurred |
| Comparative Example 4 | HDP-40 | 12.0 | 54.5 | 2.73 | Occurred |
| Comparative Example 5 | No coat | (0) | 12.2 | 3.23 | None |

EXAMPLE 5

N-methyl-N-hydroxyethylamino-2-hydroxypropyl methacrylate (hereinafter referred to as GM) was synthesized from glycidyl methacrylate and N-methyl-N-hydroxyethylamine by the same method as for the GA synthesis in Example 1.

A polymer was synthesized from GM and HEMA by the same polymerization method as in Example 1. The GM content of the obtained polymer was about 25 mol % (this polymer is hereinafter referred to as HGMA-25). The process of Example 1 was repeated except for coating a filter with this polymer by the same method as in Example 1. The average density of hydrophilic basic groups (N-methyl-N-hydroxyethylamino groups) introduced onto the filter medium surface was 7.7 $\mu$eq/m$^2$, the time required for filtering the blood was 11.8 minutes, and the leukocyte-removing capability was 4.54. The filter medium after the filtration of the blood had almost no red cells adhering thereto.

EXAMPLE 6

A polymer was synthesized from GA, HEMA and methyl methacrylate (hereinafter referred to as MMA) by the same polymerization method as in Example 1. The obtained polymer had a GA content of about 20 mol % and HEMA and MMA contents each of about 40 mol %, as measured by acid-base titration, nuclear magnetic resonance spectroscopy (NMR) and elemental analysis (this polymer is hereinafter referred to as HMGA-20). The process of Example 1 was repeated except for coating a filter with this polymer by the same method as in Example 1. The average density of the hydrophilic basic groups introduced onto the filter medium surface was 6.5 $\mu$eq/m$^2$, the time required for filtering the blood was 13.4 minutes, and the leukocyte-removing capability was 4.87. The filter medium after the filtration of the blood had almost no red cells adhering thereto.

EXAMPLE 7

To a solution of triethylene glycol monomethyl ether in pyridine, the concentration of which had been adjusted to 0.1 mol/L, thionyl chloride was slowly added to a concentration of 0.13 mol/L with cooling, and the resulting mixture was stirred at room temperature for about 1 hour. Water and diluted sulfuric acid were added thereto with cooling to decompose the excess thionyl chloride, after which the reaction product was extracted with chloroform. The extract solution was washed with a saturated aqueous sodium hydrogencarbonate solution and then distilled under reduced pressure. Thus, a compound formed by the replacement of the terminal hydroxyl group by a chlorine atom was synthesized. N-methylallylamine (0.1 mol) was dissolved in 50 mL of absolute ethanol and the resulting solution was cooled, to which the above-mentioned chlorinated compound (0.1 mol) was then added and stirred for 30 minutes to synthesize a polymerizable monomer having an ethylene oxide chain as hydrophilic portion and an amino group as basic portion (this monomer is hereinafter referred to as EA).

A polymer was synthesized from EA and HEMA by the same polymerization method as in Example 1. The EA content of the obtained polymer was about 25 mol % (hereinafter this polymer is referred to as HEA-25). The process of Example 1 was repeated except for coating a filter with this polymer by the same method as in Example 1. The average density of hydrophilic basic groups introduced onto the filter medium surface was 6.3 $\mu$eq/m$^2$, the time required for filtering the blood was 12.1 minutes, and the leukocyte-removing capability was 4.07. The filter medium after the filtration of the blood had almost no red cells adhering thereto.

EXAMPLE 8

Polyester nonwoven fabric (5 g) having an average fiber diameter of 1.2 $\mu$m was immersed in a 10% aqueous tertiary butanol solution (300mL) containing 6mL of methacrylic acid. This sample solution was irradiated with about 1 kGy of Y-rays to graft polymerize methacrylic acid onto the surface of the nonwoven fabric. The nonwoven fabric irradiated with Y-rays was washed with methanol with shaking at room temperature for 10 minutes and then with warm water of 40° C. with shaking for 2 hours. This nonwoven fabric subjected to the graft polymerization was dried in vacuum at 40° C. for 16 hours and then immersed in a chloroform solution containing triethanolamine at a concentration of 0.02 mol/L. Sulfuric acid was added thereto and the resulting mixture was heated under reflux for 6 hours. By the above procedure, esterification is caused between carboxyl groups on the surface of the nonwoven fabric and the hydroxyl groups of triethanolamine to prepare a leukocyte-removing filter medium having hydrophilic basic groups (bis(hydroxy-ethyl)amino groups) on the surface. The density of the hydrophilic basic groups introduced onto the filter medium surface was 6.9 $\mu$eq/m$^2$.

The obtained filter medium was packed into a container having an effective filtration sectional area of 67 mm×67 mm, to a thickness of 3.0 mm at a packing density of about 0.20 g/cm$^3$. On the filter medium, nonwoven fabric with an average fiber diameter of about 1.8 $\mu$m not subjected to graft polymerization was packed into the container to a thickness of 1.5 mm to produce a filter apparatus.

Using this filter apparatus, the same red cell concentrate was filtered by the same procedure as in Example 1 and the time required for filtering the blood was found to be 12.3 minutes and the leukocyte-removing capability was 4.39. The filter medium after the filtration of the blood had almost no red cells adhering thereto.

EXAMPLE 9

The same polyester nonwoven fabrics with average fiber diameters of 1.8 $\mu$m and 1.2 $\mu$m, respectively, as in Example 1 were packed into a container having an effective filtration sectional area of 67 mm×67 mm, at a packig density of 0.24 g/cm$^3$. The nonwoven fabric with an average fiber diameter of 1.8 $\mu$m was placed on the blood inlet side to a thickness of about 0.5 mm, and beneath this nonwoven fabric, the nonwoven fabric with an average fiber diameter of 1.2 $\mu$m was placed to a thickness of about 4.7 mm. The container was filled with a 0.5 wt % ethanolic solution of HGA-25 polymer and allowed to stand for 1 minute. Then, the excess solution was blown off with nitrogen gas and the container was dried in vacuum at 45° C. for 16 hours to produce a filter apparatus. The leukocyte-removing filter medium in thus produced filter apparatus had hydrophilic basic groups on its surface at an average introduction density of 16.8 $\mu$eq/m$^2$.

Minute aggregates contained in CPD-containing fresh human whole blood (hematocrit 39%) preserved at room temperature for 16 hours after blood-collecting, were removed by the same procedure as in Example 1. Then, 515 g of the human whole blood was filtered by the use of the prepared filter apparatus at a head of 0.7 m. The temperature of the CPD-containing fresh human whole blood immediately before starting the filtration was 25° C. The concentration of activated complement C3a and the amount of Factor VIII as a blood coagulation factor, were measured besides the blood filtration time and the leukocyte-removing capability.

As a result, it was found that the filtration time was 19.6 minutes and the leukocyte-removing capability was 4.18. The concentration of C3a and the amount of Factor VIII in the recovered fluid were not different from those in the fluid before filtration.

COMPARATIVE EXAMPLE 6

Using the same filter apparatus as in Example 9 except that it was obtained by coating with a 0.5 wt % ethanolic solution of HDE-25 polymer, CPD-containing fresh human whole blood was filtered by the same method as in Example 9. The average density of basic groups introduced onto the filter medium surface was 18.6 $\mu$eq/m$^2$.

As a result, the filtration time was 24.5 minutes and the leukocyte-removing capability was 3.73. As compared with the fluid before filtration, the concentration of C3a in the recovered fluid was approximately doubled and the amount of Factor VIII was decreased about 30%.

What is claimed is:

1. A leukocyte-removing filter medium for removing leukocytes from a leukocyte-containing fluid, wherein said filter medium has, at least on its surface, hydrophilic basic groups containing at least one nonionic hydrophilic portion and at least one basic portion, in which said hydrophilic portion(s) is located nearer to the end of the hydrophilic basic group than said basic portion(s) is.

2. A leukocyte-removing filter medium according to claim 1, wherein said hydrophilic portion(s) is located at the extreme end of the hydrophilic basic group.

3. A leukocyte-removing filter medium according to claim 1 or 2, wherein said hydrophilic portion(s) is a hydroxyl group.

4. A leukocyte-removing filter medium according to claim 1, wherein said basic portion(s) is a secondary amino group and/or a tertiary amino group.

5. A leukocyte-removing filter medium according to claim 1, wherein said hydrophilic basic groups are hydroxyalkylamino groups.

6. A leukocyte-removing filter medium according to claim 5, wherein the number of carbon atoms of the alkyl portion of said hydroxyalkylamino group is not more than 10 and not less than 1.

7. A leukocyte-removing filter medium according to claim 1, which has a polymerizable monomer having one or more hydrophilic basic groups, introduced onto the surface of the filter medium.

8. A leukocyte-removing filter medium according to claim 1, which has a polymer comprising units of a polymerizable monomer having one or more hydrophilic basic groups, introduced onto the surface of the filter medium.

9. A leukocyte-removing filter medium according to claim 8, wherein said polymer is a copolymer of the polymerizable monomer containing one or more hydrophilic basic groups and one or more other polymerizable monomers containing no hydrophilic basic group.

10. A leukocyte-removing filter medium according to any one of claims 7 to 9, wherein the polymerizable monomer containing one or more hydrophilic basic groups is a (meth) acrylic acid derivative.

11. A leukocyte-removing filter medium according to claim 7 or 8, wherein the polymerizable monomer having one or more hydrophilic basic groups or the polymer comprising units of a polymerizable monomer having one or more hydrophilic basic groups is introduced by a graft method and/or a coating method.

12. A leukocyte-removing filter medium according to claim 1, which has hydrophilic basic groups introduced onto the surface of filter medium by bonding of a chemical species containing the hydrophilic basic groups to active groups on the surface of a base material which forms the filter medium.

13. A leukocyte-removing filter medium according to claim 12, wherein the chemical species containing the hydrophilic basic groups is a hydroxyalkylamine.

14. A leukocyte-removing filter medium according to claim 12, wherein the active groups are of at least one kind selected from the group consisting of epoxy group, carboxyl group and acid halides.

15. A leukocyte-removing filter medium according to claim 1, wherein the density of the hydrophilic basic groups introduced per unit surface area is less than 1000 $\mu$eq/m$^2$ and not less than 0.1 $\mu$eq/m$^2$.

16. A leukocyte-removing filter medium according to claim 1, wherein the ratio of the number of the basic portion(s) to the number of the hydrophilic portion(s) is less than 0.5 and not less than 0.01.

* * * * *